United States Patent [19]

Radebaugh et al.

[11] Patent Number: 4,806,359

[45] Date of Patent: Feb. 21, 1989

[54] IBURPROFEN SUSTAINED RELEASE MATRIX AND PROCESS

[75] Inventors: Galen W. Radebaugh, Maple Glen; Robert Glinecke, Glenside; Thomas N. Julian, Horsham, all of Pa.

[73] Assignee: McNeilab, Inc., Spring House, Pa.

[21] Appl. No.: 41,164

[22] Filed: Apr. 22, 1987

[51] Int. Cl.[4] ................................................. A61K 9/26
[52] U.S. Cl. .................................... 424/470; 424/472; 427/3
[58] Field of Search ...................... 424/469, 470, 472; 427/3

[56] References Cited

U.S. PATENT DOCUMENTS

| | | | |
|---|---|---|---|
| 4,264,573 | 4/1981 | Powell et al. | 424/80 X |
| 4,465,660 | 8/1984 | David et al. | 424/15 |
| 4,684,516 | 8/1987 | Bhutani | 424/471 X |
| 4,753,801 | 1/1988 | Oren et al. | 424/465 |

OTHER PUBLICATIONS

Chowhan, Z. T. et al, *Hardness Increase Induced by Partial Moisture Loss in Compressed Tablets and Its Effect on in vitro Dissolution*, Feb. 1, 1978.

*Primary Examiner*—Michael Lusignan
*Attorney, Agent, or Firm*—Joseph J. Brindisi

[57] ABSTRACT

An ibuprofen-sustained release tablet or tablet layer is formed by making a wet granulation using providone (PVP) in alcohol as the granulating fluid which is mixed with ibuprofen, ethylcellulose, a wicking agent e.g. microcrystalline cellulose, an erosion promoter e.g. pregelatinized starch, then drying and milling the granulation and blending with dry powdered erosion promotor, wicking agent, lubricant e.g. magnesium stearate and glidant e.g. silicon dioxide, and compressing the resultant granulation, which upon administration results in a long-lasting slow and relatively regular incremental release of the ibuprofen.

19 Claims, 1 Drawing Sheet

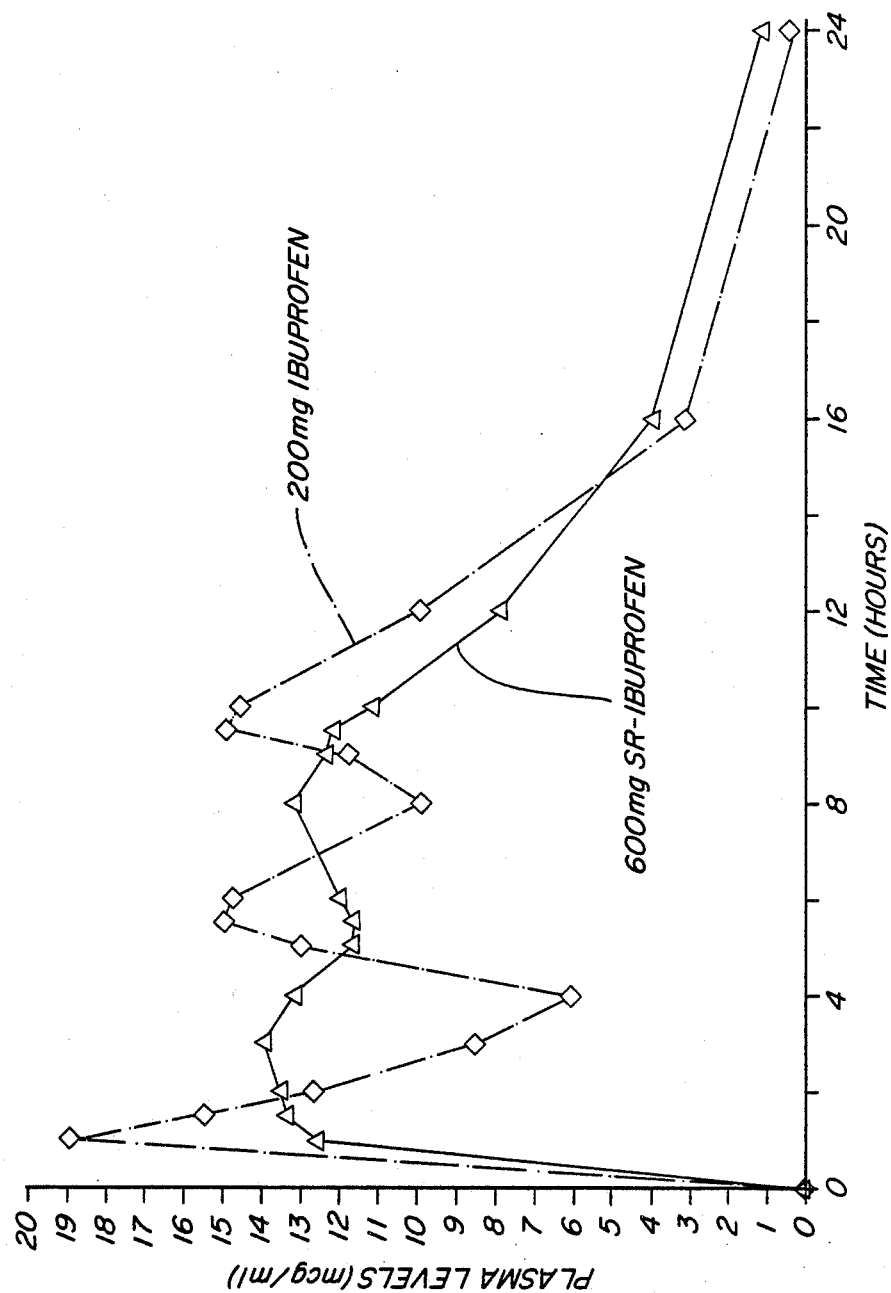

IBURPROFEN SUSTAINED RELEASE MATRIX AND PROCESS

This invention relates to a sustained release form of ibuprofen, and is more particularly concerned with an ibuprofen-containing matrix formed from granulations of ibuprofen mixed with inactive powdered excipients plus ethylcellulose using an aqueous-alcoholic solution of Povidone U.S.P. (polyvinylpyrrolidone-PVP) as the granulating fluid, which granulations are dried, milled, blended with additional inactive powdered excipients, and then compressed into a tablet, and to the process of making the ibuprofen-containing matrix in a manner so that the rate of release of ibuprofen can be easily varied or controlled.

BACKGROUND OF THE PRESENT INVENTION

Ibuprofen is a very well-known anti-inflammatory and analgesic drug. In the United States, it is available in dosage forms of 400 mg., 600 mg., and 800 mg. tablets by prescription, and as 200 mg. tablets for non-prescription over-the-counter sales. For treatment with ibuprofen over a long period of time, e.g., over 12 hours, the patient now must typically take one 200 mg. tablet or caplet, another four hours later, and a third four hours after that. In doing so, the levels of the ibuprofen in blood plasma will reach peak levels shortly after the ibuprofen tablets are taken, and then the plasma levels will decrease fairly rapidly. It would obviously be better to reduce the number of peaks and valleys so as to have a more uniform rate of release of ibuprofen into the blood plasma leading to more uniform or constant concentrations of ibuprofen in the plasma. A way to do this has now been found in a more convenient manner, using the present invention, whereby a single 600 mg. tablet or caplet can be formulated which has a sustained rate of release resulting in much more even plasma levels over twelve (12) hours, as contrasted to three (3) 200 mg. tablets or caplets. In addition, the quantity (amount) of the matrix can be adjusted up or down to produce tablets for sustained release that have more than or less than 600 mg. of ibuprofen. For example, a table containing 800 mg. of ibuprofen can be manufactured from the same composition by simply increasing the size and weight of the final tablet by a multiple of 4/3. The present invention can be utilized to obtain any desired sustained release ibuprofen tablets of different dosages, e.g. an 800 mg. sustained release tablet which results in higher blood plasma levels over twelve (12) hours, than with the 600 mg. tablets, desired longer or shorter time periods e.g. eight (8) hours are possible. From a practical standpoint twelve (12) hours might be the most desired interval. The matrix of the present invention can be utilized to make ibuprofen sustained release pharmaceutical preparations in compressed tablet form. The matrix materials used are compressed into a shaped tablet form. The term "tablet" as used herein includes tablets of any shape, and includes caplets, which are tablets having a capsule shape.

PRIOR ART

Both ethylcellulose and polyvinylpyrrolidone have been used in pharmaceutical compositions, such as tablets, including sustained release compositions. Ethyl cellulose is often used as a coating for particles or in combination with another polymer. Ethyl cellulose and PVP have even been used together, e.g., in German Offenlegusgsschrift DE No. 3331262A1, published Mar. 1, 1984, dealing with a food supplement which contains in addition to various amino acids and other ingredients both PVP and ethyl cellulose. The PVP and ethylcellulose are there used in different amounts with different other materials to make a completely different type of final product than in the instant invention.

Controlled release formulations of ibuprofen are known. Dunn et al. U.S. Pat. No. 4,308,251 (Example 38) discloses ibuprofen controlled-release tablets containing in carefully controlled amounts, both an erosion-promoter agent, specifically, corn starch, and a release-controlling agent, specifically, cellulose acetate phthalate. The process disclosed is to intimately mix the ibuprofen with the corn starch, and to add to this a solution of ethanol+methylene chloride containing cellulose acetate phthalate to form granules, which are dried, blended with colloidal silicon dioxide, and compressed into tablets. The Dunn et al. patent suggests at column 5 that (1) while the preferred release controlling agent is cellulose acetate phthalate, various other suitable agents may be used, including ethyl cellulose, and (2) while the preferred erosion-promoting agent is corn starch, various other suitable agents may be used including various vegetable starches, cellulose derivatives and cross-linked polyvinylpyrrolidone. The instant invention utilizes some of these suggested alternative ingredients in a different manner, (in the instant invention the ethyl cellulose is mixed with ibuprofen as a dry powder while the polyvinylpyrrolidone [which is a non-crosslinked PVP, and is a completely different material with different properties than the Dunn, et al. material] is dissolved in alcohol, which is the opposite of what Dunn et al. teaches) and in different proportions to make a different type of controlled-release tablet than Dunn et al.

BRIEF DESCRIPTION OF THE DRAWING

The drawing is a graphic representation of the concentration of ibuprofen in the blood plasma of test subjects over a period of 12 hours.

DISCUSSION OF PRESENT INVENTION

The ibuprofen sustained release matrix pharmaceutical tablets of the present invention are made by adding granulating fluid to a dry powder blend of active drug and inactive excipients to form wet granulations, which are then dried and finely divided, e.g., by being milled into powder form and then blended with additional inactive powdered excipients and compressed into tablets. They can be easily manufactured using conventional tabletting equipment.

The tablets of the present invention have many advantageous features. They are bioerodible when swallowed, leaving no insoluble tablet shaped device to be excreted or removed from the body. The ibuprofen sustained release matrix uses ethyl cellulose (Ethylcellulose NF) and povidone (Povidone USP) (Plasdone* K29/32) as the Matrix Binding Agents for obtaining the sustained release effect. This combination of two well-known relatively inexpensive, pharmaceutically acceptable polymers, in the relative proportions here used and in the manner here used is believed to be a major novel feature of the present invention. In the most preferred embodiments of the invention, the amount of ethylcellulose used is on the general order of two percent or less of the amount of ibuprofen, while the amount of povidone is on the general order of four percent or less of the amount of ibuprofen used. This means that the ibuprofen sustained release matrix of the present invention is capable of producing dosage forms having very high drug/matrix binding agent ratios. This results in reducing the size or number of tablets needed, making the product less expensive and more desirable to the consumer.

An advantage of the process of this invention is that the rate of matrix erosion when the tablet is swallowed can be modified so that the degree and/or length of the sustained release effect of the matrix can be easily modified by simply altering the levels of the other excipients, aside from the ethylcellulose and the povidone (PVP). Thus, the rate of release of ibuprofen from the tablet for absorption into the bloodstream can be modified to match the desired blood plasma concentration versus time profile.

The ibuprofen sustained release matrix of the present invention can be used alone as a tablet (or caplet, which is a tablet shaped like a capsule), or as part of a multi-layered tablet. Sometimes it is desirable to have a multi-layered tablet with an immediate or quick-release layer to begin raising the blood levels of ibuprofen relatively quickly until the sustained release portion of the tablet can begin to take over the effect. Thus, one can use the present invention to have two or more layers, each with a significantly different release rate of the same component or different components where a combination of drugs is desired.

In our currently preferred embodiments, the ibuprofen-sustained release matrix tablets of the present invention contain approximately 1.4 percent ethylcellulose and approximately 2.8 percent PVP, with the balance consisting of various pharmaceutically acceptable, common excipients. The tablets of the present invention have a very high drug-to-excipients ratio on the order of at least 80 percent ibuprofen to 20 percent excipients by weight. This results in a drug to total matrix weight ratio of approximately 1:1.2.

In addition to the ethylcellulose and PVP polymers discussed above which are Matrix Binding Agents, the commonly used excipients which are granulated with the ibuprofen include a wicking agent (to wick fluids into the matrix) such as microcrystalline cellulose and an "erosion promoter" such as Pregelatinized Starch. Additional excipients which are added to the granulated and dried ingredients include a wicking agent such as microcrystalline cellulose, an erosion promoter such as Pregelatinized Starch, a lubricant such as magnesium stearate and a glidant, such as colloidal silicon dioxide.

The lubricant optionally may be omitted, but is a currently preferred ingredient.

For each of the ingredients used in the sustained release matrix of the present invention, aside from the ibuprofen, the ethylcellulose and the Povidone (PVP), there exists less preferred alternative or equivalent materials which could be used in its place. The following Table I lists: each of the various preferred ingredients, the purpose of the ingredient, the preferred weight of such preferred ingredient, the usable weight range of the preferred ingredient, other less preferred alternatives or equivalents which can be substituted for the preferred ingredient, the preferred weight of such alternate ingredient and the usable weight range of such alternate ingredient for a sustained release layer containing 440 mg. of ibuprofen. [For tablets (caplets) of a higher or lower level of ibuprofen, the amounts of ingredients and their ranges would be proportionately increased or decreased.] Table 1 indicates preferred ingredients and weight ranges based upon 440.0 mg. of ibuprofen to produce sustained release tablets or caplets with a total compositional weight of from 471 to 602 mg. The preferred percent range of ibuprofen to total compositional weight is thus in the range of from 440/471 to 440/602 mg or from about 73 to about 93% by weight of ibuprofen to the total composition.

The ingredients are listed in Table I under part I Active & Excipients, Part II Granulating Agent, Part III Excipients, since they are used in this manner in the process by which the tablets of the present invention are made.

The preferred process which is utilized to form the most preferred ibuprofen-sustained release matrix of the present invention is to mix together the dry powdered active drug, ibuprofen, the dry powdered matrix binding polymer, ethyl cellulose, and the dry powdered excipients, microcrystalline cellulose and pregelatinized starch in a mixer/granulator. A granulating agent (fluid or solution) is formed by mixing alcohol (ethanol) and water to obtain a 1:1 mixture, into which Povidone is dissolved to obtain a 12.25 percent (weight-by-weight) solution. The resultant granulating agent is sprayed onto the above admixed powders while they are being mixed in the mixer/granulator so as to form a wet granulation. The wet granulation thus obtained is dried and milled. At this point a small amount of dry powdered excipients such as pregelatinized starch, microcrystalline cellulose, magnesium stearate, and colloidal silicon dioxide are added and mixed with the milled granulations, after which they are compressed thereby forming the sustained release matrix.

TABLE I

| Preferred Ingredient | Purpose | Wt./Tablet (mg) | (mg) Wt. Range | Alt./or Equiv. | Wt./Tablet (mg.) | (mg) Wt. Range |
|---|---|---|---|---|---|---|
| SUSTAINED RELEASE IBUPROFEN | | | | | | |
| *Part I - Active & Excipients* | | | | | | |
| Ibuprofen USP | Active Drug | 440.0 | — | — | — | — |
| Ethylcellulose NF (Ethocel*N-10) | Matrix Binding Agent | 7.3 | 3–12 | | | |
| Microcrystalline Cellulose NF (Avicel°) pH 101, 102, 103 105 | Wicking Agent | 22 | 10–35 | Powdered Cellulose (Solka Floc*) | 22 | 10–35 |
| Pregelatinized Starch NF (corn, wheat or potato source) | Erosion Promoter | 14 | 5–25 | Starch NF (corn, wheat or potato) or rice starch | 14 | 5–25 |
| *Part II - Granulating Agent* | | | | | | |

TABLE I-continued

SUSTAINED RELEASE IBUPROFEN

| Preferred Ingredient | Purpose | Wt./Tablet (mg) | (mg) Wt. Range | Alt./or Equiv. | Wt./Tablet (mg.) | (mg) Wt. Range |
|---|---|---|---|---|---|---|
| Povidone USP Plasdone/K 29/32 | Matrix Binding Agent | 14.7 | 5–30 | | | |
| Alcohol USP | Solvent | [1:1 alcohol-water 8.5.] | | Dehydrated Alcohol USP, Methyl Alcohol USP, Isopropyl Alcohol USP | | |
| Purified Water USP | Solvent | | | | | |

[alcohol can be used either alone, or with water in a ratio of up to about 1 part alcohol to 2 parts water]

Part III - Excipient

| Preferred Ingredient | Purpose | Wt./Tablet (mg) | (mg) Wt. Range | Alt./or Equiv. | Wt./Tablet (mg.) | (mg) Wt. Range |
|---|---|---|---|---|---|---|
| Pregelatinized Starch NF (corn, wheat, or potato source) | Erosion Promoter | 8 | 3–20 | Starch NF (corn, wheat or potato) or rice starch | 8 | 3–20 |
| | | | | Sodium Starch Glycolate NF (Explotab*) | 4 | 1–15 |
| | | | | Croscarmellose Sodium NF (Ac Di Sol*) | 4 | 1–15 |
| | | | | Crospovidone NF (Povidone XL*) | 4 | 1–15 |
| Microcrystalline Cellulose NF | Wicking Agent | 7.3 | 3–20 | Powdered Cellulose (Solka Floc*) | 7.3 | 3–20 |
| Magnesium Stearate NF | Lubricant | 5 | 0–10 | Stearic Acid NF | 5 | 0–10 |
| Colloidal Silicon Dioxide NF (Cab-O-Sil*) | Glidant | 5 | 2–10 | Fumed Silicon Dioxide (Syloid*) | 5 | 2–10 |

The sustained release matrix of the present invention is pH independent. Hydration of the matrix by fluids in the gastrointestinal tract bioerodes the matrix allowing ibuprofen to be exposed through the bioerosion. The rate of erosion and hence the rate of dissolution controls the absorption ibuprofen and the resultant plasma concentration v. time profiles. Merely changing the amount of any of the ingredients which are used for the purpose of erosion promotion will result in change in the rate of erosion of the final tablet.

If desired, a pharmaceutically acceptable coloring agent may be added to one or more of the layers of the tablet. One way of doing this is to add a dry powdered lake to Part III of the Sustained Release Ibuprofen.

If desired, the compressed tablet may be coated with a pharmaceutically acceptable polymer, gelatin, or sugar coating.

While various listed ingredients in the specification and claims have the suffix "U.S.P." (United States Pharmacopia) or "NF" (National Formulary), this is intended only to better identify the ingredient, or its purity, and not to limit the invention in any way to the use of ingredients so marked, since identical materials are available under other designations e.g. in foreign countries.

The following examples are illustrative of the most preferred embodiments of the present invention. Any of the alternative or equivalent ingredients shown in Table I could be substituted if desired.

EXAMPLES

EXAMPLE I

Ibuprofen Sustained Release Bi-Layer Tablet

This example illustrates a bi-layer tablet in which there is both an immediate release layer and a sustained release layer. The immediate release layer is analogous in composition and manufacturing procedure to currently available over-the-counter ibuprofen non-sustained release tablets, except the amount of ibuprofen in this layer of this example is 160 mg instead of 200 mg. It is the sustained release layer, which utilizes the matrix of the present invention.

The bi-layer tablet uses the following ingredients:

| Ingredient | mg/Tablet |
|---|---|
| A. Immediate Release Layer | |
| Part I Active and Excipients | |
| Ibuprofen USP | 160.0 mg |
| Microcrystalline Cellulose NF (Avicel PH 101) | 32.0 mg |
| Starch NF | 32.0 mg |
| Pregelatinized Starch NF (Starch 1500) | 16.0 mg |
| Sodium Starch Glycolate NF | 6.4 mg |
| Part II Granulating Agent | |
| Hydroxypropyl methylcellulose 2910 USP (Methocel E-5) | 1.6 mg |
| Purified Water USP | q.s. |
| Part III Excipients | |
| Sodium Starch Glycolate NF (Explotab) | 1.6 mg |
| Coloidal Silicon Dioxide NF | 0.8 mg |
| Total | 250.4 mg |
| B. Sustained Release Layer | |
| Part I Active & Excipients | |
| Ibuprofen USP | 440.0 mg |
| Ethylcellulose NF (Ethocel N-10) | 7.3 mg |
| Microcrystalline Cellulose NF (Avicel PH 101) | 22.0 mg |
| Pregelatinized Starch NF (Starch 1500) | 14.0 mg |
| Part II Granulating Agent | |
| Povidone USP (Plasdone K 29/32) | 14.7 mg |
| Alcohol USP } 1:1 mixture | q.s. |
| Purified Water USP | |
| Part III Running Powder | |
| Pregelatinized Starch NF | 8.0 mg |

-continued

| Ingredient | mg/Tablet |
|---|---|
| (Starch 1500 LM) | |
| Microcrystalline Cellulose NF (Avicel PH 101) | 7.3 mg |
| Magnesium Stearate NF | 5.0 mg |
| Colloidal Silicon Dioxide NF (Cab-O-Sil) | 5.0 mg |
| Total | 523.3 mg |
| Total Tablet Weight | 773.7 mg |

The above ingredients are utilized to make a bi-layer tablet to the following working directions:

WORKING DIRECTIONS

A. Immediate Release Layer

1. Weigh the components of Part I and preblend them in a high shear mixer (Fielder: impeller speed of approximately 118 RPM for 3 minutes).
2. Prepare the granulating agent (Part II) by dissolving the Hydroxypropyl Methylcellulose 2910 USP into the Purified Water USP (a ratio of 3.2 grams of hydroxypropyl methylcellulose to 200 grams water).
3. Deliver the granulating agent to the powders of Part I, in the high shear mixer. Granulate the mixture for 20 minutes (Fielder: impeller speed of approximately 118 RPM).
4. Remove the completed wet granulation from the high shear mixer and load into the product bowl of a fluid bed apparatus (e.g. Aeromatic or Glatt). With an inlet air temperature of approximately 60° C., dry the granulation to a moisture level of 0.5 to 1.1% as determined by loss on drying (e.g. Computrac). The wet granulation can also be dried on trays in drying ovens.
5. Sieve the dried granulation (e.g. Glatt Quick Sieve: Stator No. 3, Screen No. 1.5 mm, 1000 RPM). Other machines such as a Fitzpatrick Communition Mill can be used.
6. Blend the sieved and dried granulation with the powders of Part III using a suitable mixer such as a twin-shell, ribbon or planetary mixer.

B. Sustained Release Layer

1. Weigh the components of Part I and preblend them in a high shear mixer (Fielder: impeller speed of approximately 250 RPM for 1 minute).
2. Prepare the granulating agent (Part II) by dissolving the Povidone USP in a 1:1 mixture of alcohol USP and purified water USP (a ratio of 12.25 grams of povidone to 100 grams of alcohol/water).
3. Spray the granulating agent at a rate of 600 ml/min. onto Part I in the high shear mixer. Granulate the mixture for one minute after the addition of Part II (Fielder: impeller speed of approximately 250 RPM).
4. Remove the completed wet granulation from the high shear mixer and load it into the product bowl of a fluid bed apparatus (e.g. Aeromatic or Glatt). With an inlet air temperature of approximately 60° C., dry the granulation to a moisture level of 0.3 to 0.8% as determined by loss on drying (e.g. Computrac). The wet granulation can also be dried on trays in drying ovens.
5. Sieve the dried granulation (Fitzpatrick Communition Mill, Model D6: medium speed, knives forward, 0.093 screen). Other machines such as Glatt Quick Sieve can also be used.
6. Blend the sieved and dried granulation with the powders of Part III using a suitable mixer such as a twin-shell, ribbon or planetary mixer.

C. Compression of Tablets or Caplets

1. Load the granulation of the immediate release layer into one hopper and the granulation of the sustained release layer into the second hopper of a bilayer tableting machine (e.g. Stokes Versapress). Compress tablets using 0.749×0.281×0.060 extra deep concave capsule shaped tooling. (Tablet tooling of other shapes such as oval or round can also be used). The sustained release layer has a target weight of 523.3 mg. and the immediate release layer has a target weight of 250.4 mg. Ideal tablet hardness immediately after compression is 11 to 12 Kp.

The tablets of Example I were tested in twelve adult human male subjects and compared to non-sustained release (immediate release only) tablets in a cross-over design. A single tablet of Example I, which contained 600 mg. of ibuprofen, was dosed at time=0 hour. The non-sustained tablets, each containing 200 mg. ibuprofen, were dosed at time=0 hours, 4 hours and 8 hours. Subjects were fasted 8 hours prior to administration of the first dose. Blood samples were taken from each subject, in each dosing regimen at 0, 1, 1.5, 2, 3, 4, 5, 5.5, 6, 8, 9, 9.5, 10, 12, 16 and 24 hours. Plasma was separated from the blood and the concentration of ibuprofen in each sample was determined. The results are shown numerically in Tables 2a, and 2b and graphically in the drawing. The results show that one bi-layer tablet of Example 1 reduces the number of peaks and valleys of the plasma concentration versus time profile and provides equivalent area under the curve (AUC) when compared to three non-sustained release tablets, each containing 200 mg. ibuprofen.

TABLE 2a

Sustained Release Ibuprofen 600 mg. (Example 1) Average Plasma Concentration Levels of Ibuprofen (mcg/ml) in twelve subjects. Average AUC equaled 174 mcg/hr.

| TIME (Hours) Post Dosing | | | | | | | | | | | | | | | |
|---|---|---|---|---|---|---|---|---|---|---|---|---|---|---|---|
| 0 | 1.0 | 1.5 | 2.0 | 3.0 | 4.0 | 5.0 | 5.5 | 6.0 | 8.0 | 9.0 | 9.5 | 10. | 12 | 16 | 24 |
| Average (mcg/ml) | | | | | | | | | | | | | | | |
| 0 | 12.3 | 12.6 | 13.7 | 11.5 | 9.7 | 9.2 | 9.6 | 9.9 | 11.6 | 11.4 | 11.4 | 11.7 | 8.8 | 4.0 | 1.5 |

TABLE 2b

Non-sustained Release Ibuprofen 200 mg. Tablets; Average Plasma Concentration Level of Ibuprofen (mcg/ml) for dosing at 0, 4 and 8 hours in twelve subjects. Average AUC Equaled 180 mcg/hr.

| TIME (Hours) Post Dosing | | | | | | | | | | | | | | | |
|---|---|---|---|---|---|---|---|---|---|---|---|---|---|---|---|
| 0 | 1.0 | 1.5 | 2.0 | 3.0 | 4.0 | 5.0 | 5.5 | 6.0 | 8.0 | 9.0 | 9.5 | 10. | 12 | 16 | 24 |

TABLE 2b-continued

Non-sustained Release Ibuprofen 200 mg. Tablets; Average Plasma Concentration Level of Ibuprofen (mcg/ml) for dosing at 0, 4 and 8 hours in twelve subjects.
Average AUC Equaled 180 mcg/hr.

Average (mcg/ml)
0  19.1  15.4  12.5  8.5  6.0  13.0  14.9  14.7  9.9  11.8  14.9  14.6  9.9  3.1  0.3

EXAMPLE II

Ibuprofen Sustained Release Bi-layer Tablet Containing a Total of 800 mg. Ibuprofen This example illustrates a bi-layer tablet which is analogous to the tablet described in Example I, except all amounts of ingredients per tablet and final weight of the tablet are 4/3 times the amounts and final weight of Example I. The working directions for the immediate release layer and the sustained release layer are analogous to the working directions described in Example I. Tablets can be compressed using capsule, oval, round or other appropriately shaped tooling. The sustained release layer has a target weight of 697.8 mg. and the immediate release layer has a target weight of 333.8 mg.

| Ingredient | mg/Tablet |
|---|---|
| A. Immediate Release Layer | |
| Part I Active and Excipients | |
| Ibuprofen USP | 213.3 |
| Microcrystalline Cellulose NF (Avicel PH 101) | 42.7 |
| Starch NF | 42.7 |
| Pregelatinized Starch NF (Starch 1500) | 21.3 |
| Sodium Starch Glycolate NF (Explotab) | 8.5 |
| Part II Granulating Agent | |
| Hydroxypropyl Methylcellulose 2910 USP | 2.1 |
| Purified Water USP | |
| Part III Excipients | |
| Sodium Starch Glycolate NF (Explotab) | 2.1 |
| Colloidal Silicon Dioxide NF | 1.1 |
| B. Sustained Release Layer | |
| Part I Active and Excipients | |
| Ibuprofen USP | 586.7 |
| Ethylcellulose NF (Ethocel N-10) | 9.7 |
| Microcrystalline Cellulose NF (Avicel PH 101) | 29.3 |
| Pregelatinized Starch NF (Starch 1500) | 18.7 |
| Part II Granulating Agent | |
| Povidone USP (Plasdone K 29/32 | 19.6 |
| Alcohol USP (ethanol) 1:1 mixture | q.s. |
| Purified Water USP | |
| Part III Excipients | |
| Pregelarinized Starch NF (Starch 1500) | 10.7 |
| Microcrystalline Cellulose NF (Avicel PH 101) | 9.7 |
| Magnesium Stearate NF | 6.7 |
| Colloidal Silicon Dioxide NF (Cab-O-Sil) | 6.7 |
| Total | 697.8 |
| Total Tablet Weight | 1031.6 |

EXAMPLE III

Ibuprofen Sustained Release Tablet Containing 600 mg. of Ibuprofen in Matrix Form This example illustrates a mono-layer (all matrix) tablet in which there is only a sustained release layer. The working directions are analogous to the working directions for the sustained release layer described in Example I except that the amounts of all ingredients are proportionally increased such that the final tablet contains 600 mg. ibuprofen. Tablets can be compressed using capsule, oval, round or other appropriately shaped tooling. The final target weight of the compressed tablet is 713.6.

| Ingredient | Mg/tablet |
|---|---|
| Part I Active and Excipients | |
| Ibuprofen USP | 600 |
| Ethylcellulose NF (Ethocel N-10)0 | 10 |
| Microcrystalline Cellulose NF (Avicel PH 101) | 30 |
| Pregelatinized Starch NF (Starch 1500) | 19.1 |
| Part II Granulating Agent | |
| Povidone USP (Plasdone K 29/32) | 20 |
| Ethanol USP | |
| Purified Water USP | |
| Part III Excipients | |
| Pregelatinized Starch NF (Starch 1500) | 10.9 |
| Microcrystalline Cellulose NF (Avicel PH 101) 1:1 mixture | 10 |
| Magnesium Stearate NF | 6.8 |
| Colloidal Silicon Dioxide NF (Cab-O-Sil) | 6.8 |
| Total Tablet Weight | 713.6 |

EXAMPLE IV

Ibuprofen Sustained Release Tablet Containing 800 mg of Ibuprofen in Matrix Form This example illustrates a mono-layer (all matrix) tablet in which there is only a sustained release layer. The working which there is only a sustained release layer. The working directions are analogous to the working directions for the sustained release layer described in Example I except that the amounts of all ingredients are proportionally increased such that the final tablet contains 800 mg. ibuprofen. Tablets can be compressed using capsule, oval, round or other appropriately shaped tooling. The total tablet weight of the compressed tablet is 951.5 mg.

| Ingredient | mg/tablet |
|---|---|
| Part I Active Excipients | |
| Ibuprofen USP | 800 |
| Ethylcellulose NF (Ethocel N-10) | 13.3 |
| Microcrystalline Cellulose NF | 40 |

-continued

| Ingredient | mg/tablet |
|---|---|
| (Avicel PH 101) | |
| Pregelatinized Starch NF | 25.5 |
| (Starch 1500) | |
| Part II Granulating Agent | |
| Povidone USP | 26.7 |
| (Plasdone K 29/32) | |
| Alcohol USP } 1:1 mixture | q.s. |
| Purified Water USP | |
| Part III Excipients | |
| Pregelatinized Starch NF | 14.5 |
| (Starch 1500) | |
| Microcrystalline Cellulose NF | 13.3 |
| (Avicel PH 101) | |
| Magnesium Stearate NF | 9.1 |
| Colloidal Silicon Dioxide NF | 9.1 |
| (Cab-O-Sil) | |
| Total Tablet Weight | 951.5 |

What is claimed is:

1. The process of preparing an ibuprofen-sustained release shaped and compressed tablet characterized by a long-lasting slow and relatively regular incremental release of the ibuprofen upon administration comprising the following steps:

(A) forming a granulating agent by dissolving 5–30 parts by weight of the total composition of Povidone in alcohol or an alcohol-water mixture;

(B) blending together the following parts by weight of the total composition of ingredients with sufficient ibuprofen to comprise 73 to 93 percent by weight of the total composition in dry powder form:

| Ingredient | Parts by Weight |
|---|---|
| Ethylcellulose | 3–12 |
| wicking agent | 10–35 |
| erosion promoter | 5–25 |

(C) adding the granulating agent from Step A to the blended powders from Step B, and forming a wet granulation;
(D) drying the wet granulation of Step C;
(E) milling the dried granulation from Step D;
(F) thoroughly blending the milled dried granulation from Step E with the following parts by weight of the total composition of ingredients in dry powder form:

| Ingredient | Parts by Weight |
|---|---|
| Erosion Promoter | 1–20 |
| wicking agent | 3–20 |
| lubricant | 0–10 |
| glidant | 2–10; and |

(G) compressing the final granulation from step F into a tablet or tablet layer.

2. The process of claim 1 wherein:
in Step A the alcohol used in Alcohol USP or Dehydrated Alcohol USP or Methyl Alcohol USP or Isopropyl Alcohol USP;
in Step B the wicking agent used is Microcrystalline Cellulose or Powdered Cellulose and the erosion promoter used is Pregelantinized Starch or Starch NF or rice starch;
in Step C the wet granulation is formed by mixing in a high shear granulator; and
in Step F the Erosion Promoter used is 3–20 parts by weight of either Pregelantinized Starch or Starch NF or rice starch or is 1–15 Parts by Weight of Sodium Starch Glycolate or Croscarmellose Sodium or Crospovidone; the lubricant used is Magnesium Stearate or Stearic Acid; and, the Glidant used is Colloidal Silicon Dioxide or Fumed Silicon Dioxide.

3. The process of claim 2 wherein:
in Step A the alcohol used is Alcohol USP;
in Step B the wicking agent used is Microcrystalline Cellulose, the Erosion Promoter used is Pregelatinized Starch; in Step F the Erosion Promoter used is Pregelatinized Starch; the Lubricant used is Magnesium Stearate; and the Glidant used is Colloidal Silicon Dioxide.

4. The process of claim 3 wherein the specific ingredients and amounts used are:

| Step | Ingredient | Parts by Weight |
|---|---|---|
| A | alcohol-water (1:1) | q.s. |
| | Povidone | 14.7 |
| B | Ibuprofen | 440.0 |
| | Ethylcellulose | 7.3 |
| | Microcrystalline Cellulose | 22 |
| | Pregelatinized Starch | 14 |
| F | Pregelatinized Starch | 8 |
| | Microcrystalline Cellulose | 7.3 |
| | Magnesium Stearate | 5 |
| | Colloidal Silicon Dioxide | 5 |

5. The process of claim 4 wherein the Parts by Weight shown refer to milligrams per tablet.

6. A shaped and compressed sustained release therapeutic composition comprising ibuprofen and a granulating agent and excipients combined into a matrix, characterized by a long-lasting, slow and relatively regular incremental release of the ibuprofen upon administration, wherein the granulating agent and excipients include ethylcellulose and povidone, and wherein the total amount of granulating agent and excipients is effective to bind the ibuprofen in a sustained release solid matrix but is less than about 20 percent of the weight of said shaped and compressed composition.

7. A shaped and compressed ibuprofen sustained release tablet made by wet granulating a sufficient amount of ibuprofen to comprise from about 73 to 93 percent of the total composition with the Excipients of Part I and the Granulating Agent of Part II, drying and milling the resultant granulations, and then blending with the Excipients of Part III and compressing into a tablet, wherein the ingredients of Parts I, II and III comprise the following:

| Ingredient | Parts by Weight Range Tablet |
|---|---|
| Part I Excipients | |
| Ethyl Cellulose | 3–12 |
| Microcrystalline Cellulose | 10–35 |
| Pregelatinized Starch | 5–25 |
| Part II Granulating Agent | |
| Povidone | 5–30 |
| Alcohol or Alcohol-Water | q.s. |
| Part III Excipients | |
| Pregelatinized Starch | 3–20 |

-continued

| Ingredient | Parts by Weight Range Tablet |
|---|---|
| Microcrystalline Cellulose | 3-20 |
| Magnesium Stearate | 2-10 |
| Colloidal Silicon Dioxide | 2-10 |

8. The tablet of claim 7 wherein the Parts by Weight refer to milligrams per tablet, and wherein the ingredients are present either in the weights indicated or in such weights multiplied by an appropriate fraction.

9. A composition according to claim 6 wherein the total amount of granulating agent and excipients is greater than about 7 but less than about 20 percent of the total weight of said shaped and compressed composition.

10. A process of preparing an ibuprofen sustained release bi-layer tablet comprising a first layer of immediate release and a second layer of sustained and relatively regular incremental release of ibuprofen according to the steps of:
(A) preparing an immediate release layer comprising ibuprofen and pharmaceutically acceptable excipients; and
(B) preparing a sustained release layer comprising ibuprofen as the active ingredient according to the steps of:
(1) forming a granulating agent by dissolving about 5-30 parts by weight of the total sustained release layer of Povidone in alcohol or an alcohol-water mixture;
(2) blending together a sufficient amount of ibuprofen to comprise 73 to 93 percent of the total weight of the sustained release layer with the following ingredients in dry powder form in parts by weight of the total sustained release layer as indicated:

| Ingredient | Parts by Weight |
|---|---|
| Ethylcellulose | 3-12 |
| wicking agent | 10-35 |
| erosion promoter | 5-25 |

(3) adding the granulating agent from Step A to the blended powders from Step 2, and forming a wet granulation;
(4) drying the wet granulation of Step 3;
(5) milling the dried granulation from Step 4;
(6) thoroughly blending the milled dried granulation from Step 5 with the following ingredients in dry powder form;

| Ingredient | Parts by Weight |
|---|---|
| Erosion Promoter | 1-20 |
| wicking agent | 3-20 |
| lubricant | 0-10 |
| glidant | 2-10 |

(C) combining and compressing the immediate release layer of step A with the sustained release layer of Step B into a bi-layered tablet.

11. The process of claim 10 wherein:
in Step 1 the alcohol is Alcohol USP, Dehydrated Alcohol USP, Methyl Alcohol USP or Isopropyl Alcohol USP;
in Step 2 the wicking agent is Microcrystalline Cellulose or Powdered Cellulose, the Erosion Promoter is Pregelatinized Starch, Starch NF or rice starch; and
in Step 6 the Erosion Promoter is 3-20 parts by weight of the total sustained release layer and is either Pregelatinized Starch NF or rice starch, or is 1-15 parts by weight of the total sustained release layer and is Sodium Starch Glycolate, Croscarmellose Sodium or Crospovidone, the lubricant is Magnesium Stearate or Stearic Acid and the Glidant is colloidal Silicon Dioxide or Fumed Silicon Dioxide.

12. The process of claim 11 wherein:
in Step 1 the alcohol is Alcohol USP;
in Step 2 the wicking agent is Microcrystalline Cellulose, the Erosion Promoter is Pregelatinized Starch;
in Step 3 the wet granulation is formed by mixing in a high gear granulator; and
in Step 6 the Erosion Promoter is Pregelatinized Starch, the Lubricant is Magnesium Stearate, and the Glidant is Colloidal Silicon Dioxide.

13. The process of claim 12 wherein the specific ingredients and amounts used for the sustained release layer are:

| Step | Ingredient | Parts by Weight |
|---|---|---|
| 1 | alcohol-water (1:1) | q.s. |
|   | Povidone | 14.7 |
| 2 | Ethylcellulose | 7.3 |
|   | Microcrystalline Cellulose | 22 |
|   | Pregelatinized Starch | 14 |
| 6 | Pregelatinized Starch | 8 |
|   | Microcrystalline Cellulose | 7.3 |
|   | Magnesium Stearate | 5 |
|   | Colloidal Silicon Dioxide | 5 |

14. The process of claim 10 wherein the immediate release layer comprises a composition of the following ingredients: ibuprofen; microcrystalline cellulose; starch; sodium starch glycolate; and a granulating agent.

15. The process of claim 14 wherein the immediate release layer additionally comprises colloidal silicon dioxide and the granulating agent is hydroxypropyl methylcellulose.

16. A shaped and compressed bi-layer therapeutic composition comprising ibuprofen in a first immediate release layer and a second sustained release layer wherein the immediate release layer comprises ibuprofen and pharmaceutically acceptable excipients and the sustained release layer comprises ibuprofen, a granulating agent and excipients combined into a matrix, wherein the granulating agent and excipients of the sustained release layer include ethylcellulose and povidone, and wherein the total amount of said granulating agent and excipients is effective to bind the ibuprofen in a sustained release solid matrix but is less than about 20 percent of the weight of the sustained release layer of said shaped and compressed bi-layer composition.

17. The therapeutic composition of claim 16 wherein the immediate release layer comprises ibuprofen; microcrystalline cellulose; starch; sodium starch glycolate; and a granulating agent.

18. The therapeutic composition of claim 16 wherein the amount of granulating agent and excipients is greater than about 7 percent but less than about 20 percent of the total weight of the sustained release layer of said shaped and compressed bi-layer composition.

19. A shaped and compressed bi-layered immediate release layer and sustained release layer ibuprofen tablet made by combining an immediate release layer comprising ibuprofen and pharmaceutically acceptable excipients with a sustained release layer made by wet granulating a sufficient amount of ibuprofen to comprise 73 to 93 percent of the total weight of the sustained release layer with the Excipients of Part I and the Granulating Agent of Part II, drying and milling the resultant granulations, and then blending with the Excipients of Part III and compressing the two layers into a tablet, wherein the ingredients of Parts I, II and III comprise the following:

| Ingredient | Range of Parts by Weight of the Total Sustained Release Layer |
|---|---|
| Part I Excipients | |
| Ethyl Cellulose | 3–12 |
| Microcrystalline Cellulose | 10–35 |
| Pregelatinized Starch | 5–25 |
| Part II Granulating Agent | |
| Povidone | 5–30 |
| Alcohol or Alcohol-Water | q.s. |
| Part III Excipients | |
| Pregelatinized Starch | 3–20 |
| Microcrystalline Cellulose | 3–20 |
| Magnesium Stearate | 2–10 |
| Colloidal Silicon Dioxide | 2–10 |

* * * * *